United States Patent [19]
Racenet et al.

[11] Patent Number: 5,911,352
[45] Date of Patent: Jun. 15, 1999

[54] SURGICAL STAPLING APPARATUS

[75] Inventors: David C. Racenet, Southbury; Roman Czernik, Trumbull, both of Conn.

[73] Assignee: United States Surgical Corporation, Norwalk, Conn.

[21] Appl. No.: 08/768,351

[22] Filed: Dec. 17, 1996

[51] Int. Cl.$^6$ .................................................. A61B 17/04
[52] U.S. Cl. .................................. 227/175.1; 227/181.1; 227/19
[58] Field of Search .............................. 227/175.1, 176.1, 227/19, 181.1

[56] References Cited

U.S. PATENT DOCUMENTS

| | | |
|---|---|---|
| D. 322,143 | 12/1991 | Spreckelmeier . |
| 3,079,606 | 3/1963 | Bobrov et al. . |
| 3,490,675 | 1/1970 | Green et al. . |
| 3,499,591 | 3/1970 | Green . |
| 4,111,206 | 9/1978 | Vishnevsky et al. . |
| 4,244,372 | 1/1981 | Kapitanov et al. . |
| 4,290,542 | 9/1981 | Fedotov et al. . |
| 4,429,695 | 2/1984 | Green . |
| 4,520,817 | 6/1985 | Green . |
| 4,617,928 | 10/1986 | Alfranca . |
| 4,633,861 | 1/1987 | Chow et al. . |
| 4,633,874 | 1/1987 | Chow et al. . |
| 4,784,137 | 11/1988 | Kulik et al. . |
| 4,863,088 | 9/1989 | Redmond et al. . |
| 4,892,244 | 1/1990 | Fox et al. . |
| 4,955,959 | 9/1990 | Tompkins et al. . |
| 5,014,899 | 5/1991 | Presty et al. . |
| 5,030,111 | 7/1991 | Eastman . |
| 5,065,929 | 11/1991 | Schulze et al. . |
| 5,074,454 | 12/1991 | Peters . |
| 5,111,987 | 5/1992 | Moeinzadeh et al. . |
| 5,263,629 | 11/1993 | Trumbull et al. ......................... 227/19 |
| 5,308,576 | 5/1994 | Green et al. .............................. 227/19 |
| 5,405,072 | 4/1995 | Zlock et al. . |
| 5,452,837 | 9/1995 | Williamson, IV et al. ............... 227/19 |
| 5,480,089 | 1/1996 | Blewett . |
| 5,505,363 | 4/1996 | Green et al. .............................. 227/19 |
| 5,529,235 | 6/1996 | Boiarski et al. ..................... 227/175.1 |
| 5,641,111 | 6/1997 | Ahrens et al. ............................ 227/19 |

FOREIGN PATENT DOCUMENTS

| | | |
|---|---|---|
| 178041 | 4/1986 | European Pat. Off. . |
| 179623 | 4/1986 | European Pat. Off. . |
| 246870 | 11/1987 | European Pat. Off. . |
| 332413 | 9/1989 | European Pat. Off. . |
| 2445132 | 12/1979 | France . |
| 1198666 | 7/1970 | United Kingdom . |

*Primary Examiner*—Jessica J. Harrison
*Assistant Examiner*—John Paradiso

[57] ABSTRACT

A surgical stapling apparatus includes an anvil having a trunnion with outward facing protuberances. The anvil has planar lateral sides. A mounting bracket for attaching a handle to the anvil has planar lateral sides which are flush against the planar lateral sides of the anvil by and fixedly attached thereto by, for example, a plurality of spot welds.

21 Claims, 5 Drawing Sheets

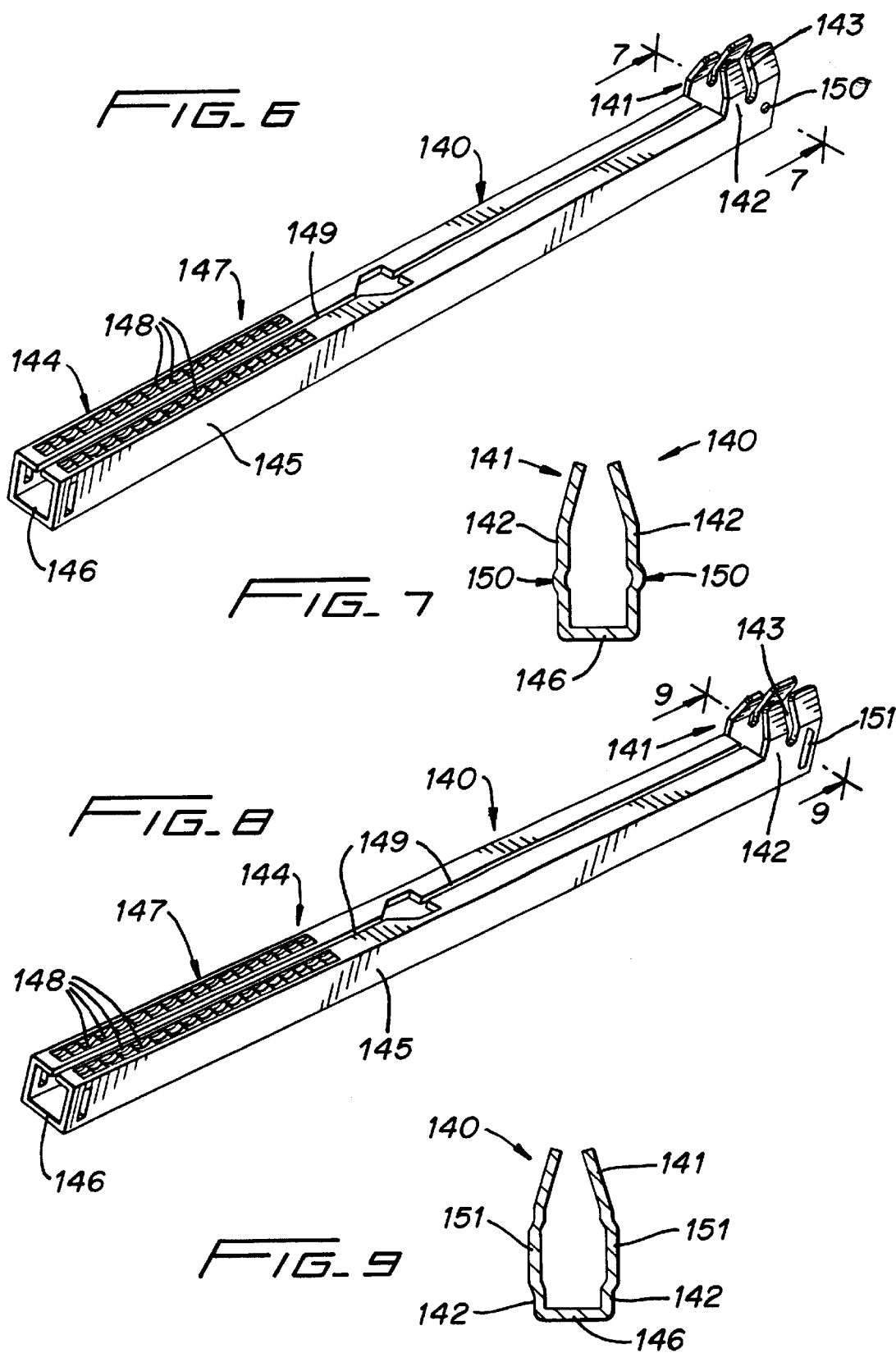

SURGICAL STAPLING APPARATUS

BACKGROUND OF THE INVENTION

1. Field of the Invention

This invention relates to an apparatus for applying surgical fasteners, and more particularly to an apparatus for resection, transection and creation of anastomoses.

2. Background of the Art

Surgical fastening apparatus for resection, transection and creation of anastomoses are used, for example, for suturing gastric and intestinal walls with spaced parallel rows of longitudinally aligned surgical fasteners or staples.

U.S. Pat. No. 3,079,606 to Bobrov et al. discloses an instrument for suturing gastric and intestinal walls with metal staples by inserting the tips of the instrument through apertures in the walls of the organs to be sutured. The apparatus includes a two part frame with each part having a finger-like projection or fork. The forks are inserted respectively into the apertures in the walls of the organs to be sutured. The frame parts are hinged together with the body tissue held between the forks. When the instrument is actuated, or "fired", longitudinally moving cam bars contact staple drive members in one of the forks, thereby pushing the surgical staples through the body tissue and into an anvil in the opposite fork by which they are crimped closed. A knife blade between the cam bars creates an incision between the parallel rows of staples. It should be noted, however, that the knife blade is an optional feature, i.e. the instrument may be used to fasten body tissue without creating an incision between the rows of staples.

U.S. Pat. No. 3,490,675 to Green et al. discloses an improvement on the instrument discussed above, whereby a double row of staples is placed on each side of the incision.

A further improvement in this type of instrument is disclosed in U.S. Pat. No. 3,499,591 to Green, which incorporates an improved structure for the staple carrying cartridge, the pusher assembly which includes the cam bars and the knife, and the staple drive members.

Generally, the above mentioned instruments are successfully used in abdominal, gynecological, pediatric and thoracic surgery. Surgical fastener applying apparatus can be used to apply metal staples, which are crimped in the anvil portion of the apparatus, or bioabsorbable fasteners, such as two-part fasteners having a fastener portion and a retainer which interlocks therewith upon firing of the instrument.

In any such instrument it is important to maintain proper alignment: alignment of the jaws of the instrument, and alignment of the tissue held between the jaws. Alignment of the instrument insures that the surgical fasteners are properly closed to achieve hemostasis. In the case of metal staples, the staples are closed when their legs are crimped in corresponding depressions, or "buckets", in the anvil. The staples are typically less than $\frac{1}{10}$" across. Misalignment between the staple legs and buckets can cause faulty crimping of the legs. Without proper closure of the staples the body tissue may be improperly sealed, possibly resulting in bleeding, infection, and added trauma.

Forces encountered during the stapling operation can contribute to misalignment. For example, if the tissue being operated upon is wedge shaped, with one side being thicker than the other, the stapler jaws will have a tendency to "roll". Deflection can also occur as a result of vertical forces applied to the anvil during contact by the fasteners. More deflection occurs at the distal end of the anvil. The longer the anvil the greater the tendency to bend. Hence, one way of dealing with bending is to limit the length of the anvil. But in many applications it is desirable to use a longer anvil, which would be able to apply longer rows of staples.

Another way of reducing bending is to make the anvil stronger. Anvils are presently fabricated by cold working sheet stainless steel of about 0.05 inches to about 0.075 inches in thickness into the desired shape. Stronger anvils can be made by increasing the thickness of the steel. However, this presents disadvantages insofar as the weight and cost of the anvil, as well as the difficulty of working thicker steel. Using an alternative harder material of construction can increase the rigidity of the anvil, but possibly at the expense of sacrificing desirable properties of the stainless steel.

Thus, alignment is affected by close mating of the parts of the apparatus, precision of the geometry of the parts, and the strength and design of the parts. An example of a surgical staplers designed to maintain alignment of tissue is disclosed in U.S. Pat. No. 5,014,899. Examples of surgical staplers designed to maintain alignment of the jaws are in U.S. Pat. Nos. 4,863,088 and 5,405,072. In particular, U.S. Pat. No. 5,405,072 discloses an anvil having lengthwise indentations on the side walls of the anvil to increase resistance to bending. U.S. Pat. No. 4,863,088 discloses a stapler having a support element 60 which engages a socket 66 in the opposing jaw part to restrict deflection of the handle parts and limit transverse deflection of the jaw parts relative to each other. The present application is directed to a surgical stapler which incorporates an alternate approach to maintaining alignment of the jaws.

SUMMARY

A surgical stapling apparatus with improved alignment is provided herein. The apparatus includes a first frame having a proximal end portion and a distal end portion and including a disposable loading unit support fixedly attached to a first handle. The apparatus further includes a second frame including a second handle pivotally mounted to a bracket which is fixedly attached to an anvil. At its proximal end, the anvil includes a trunnion portion which has two spaced apart walls, each wall having an outward facing planar surface and an outward projecting protuberance on the planar surface. The protuberances can be, for example, circular or elongated.

The anvil has planar sides which are substantially in flush contact with planar lateral sides of the bracket, these contacting sides being fixedly attached by, for example, spot welding, preferably in two or more locations on each lateral side.

BRIEF DESCRIPTION OF DRAWINGS

Various embodiments are described herein with reference to the drawings wherein:

FIGS. 6 and 7 are, respectively, perspective and sectional views of one embodiment of the anvil;

FIGS. 8 and 9 are, respectively, perspective and sectional views of an alternate embodiment of the anvil.

DETAILED DESCRIPTION OF PREFERRED EMBODIMENTS

Figure 1:
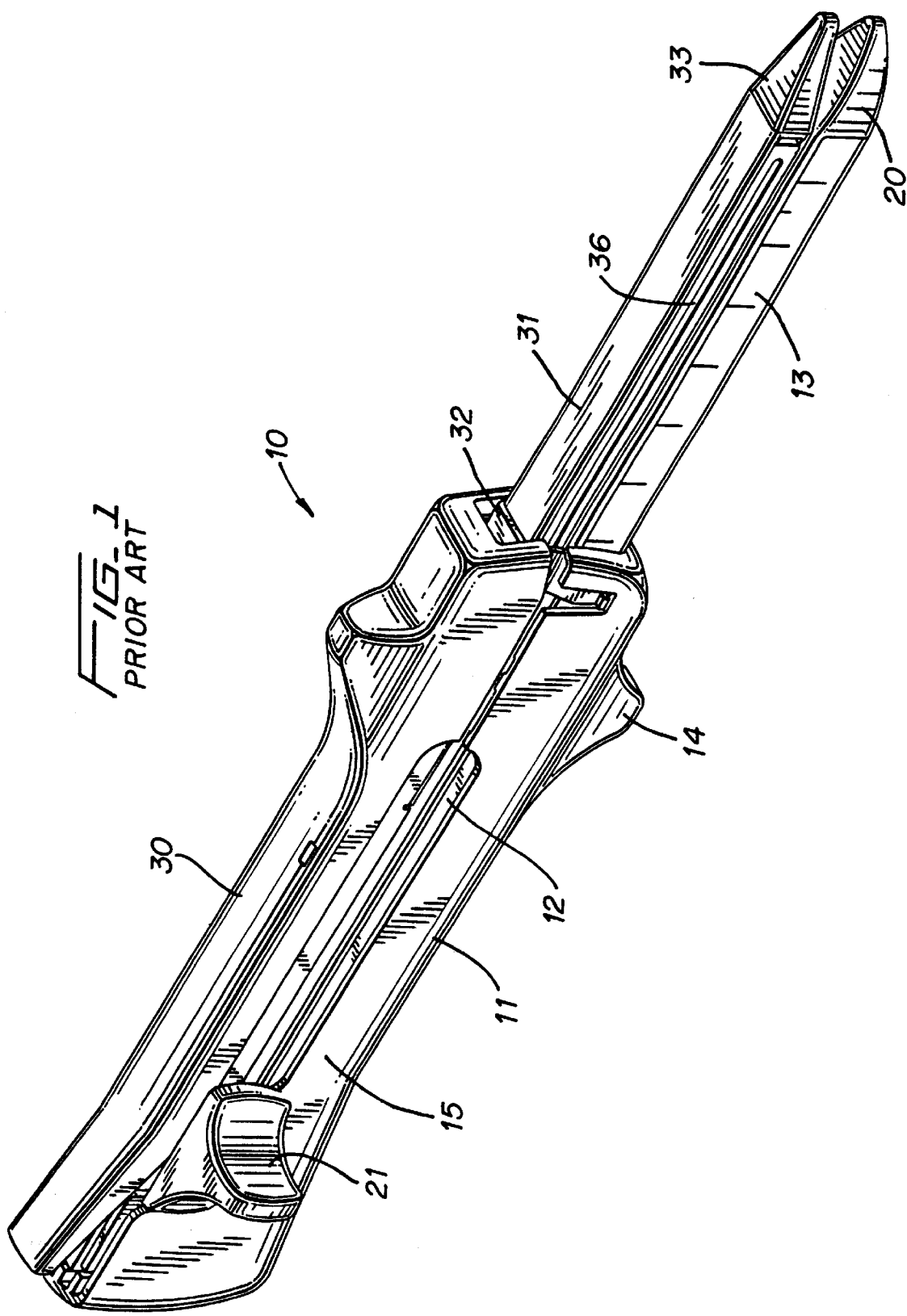
FIG. 1 is perspective view of a prior art surgical stapling apparatus.
Figure 2:
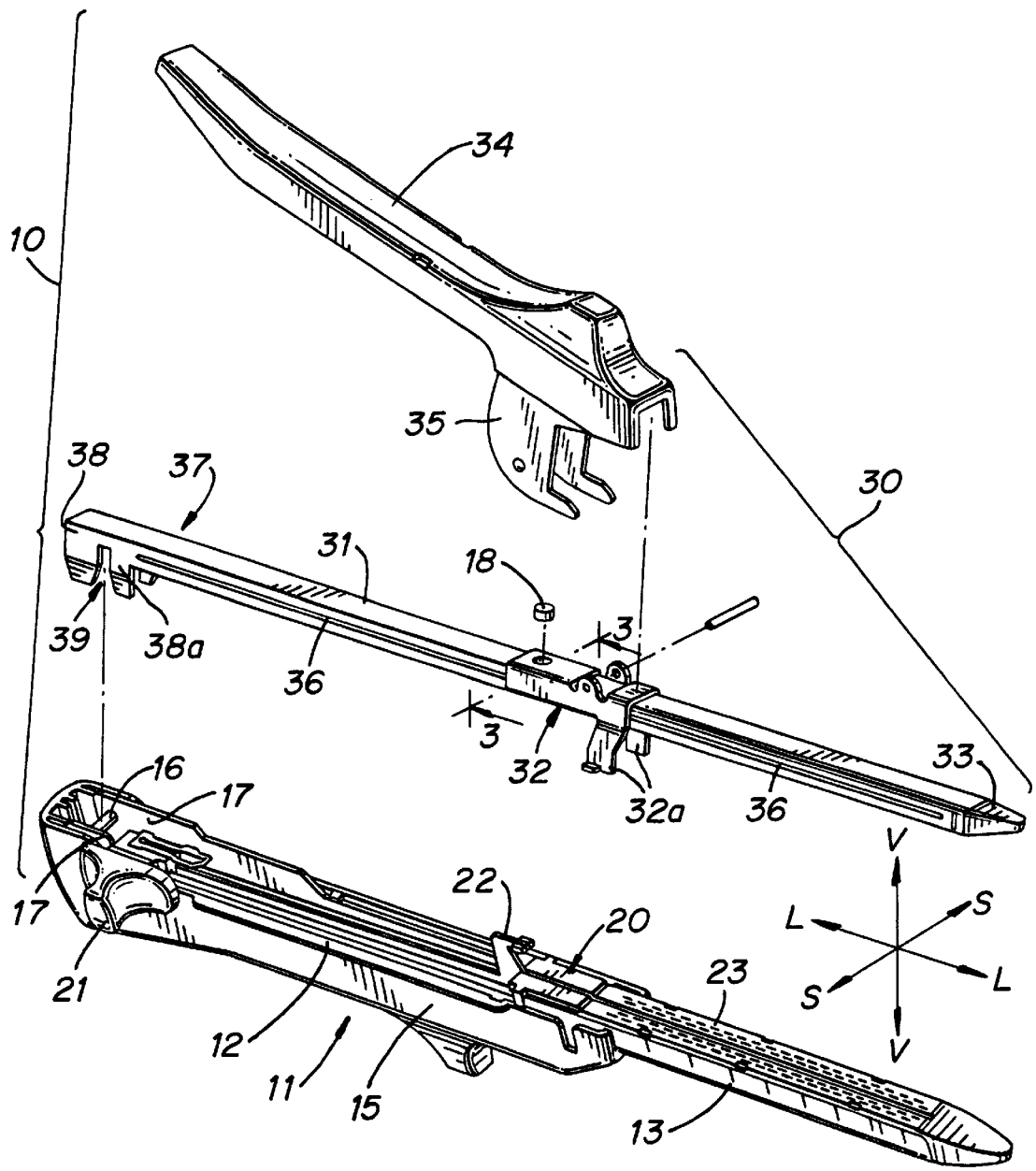
FIG. 2 is an exploded perspective view of the prior art apparatus.
Figure 3:
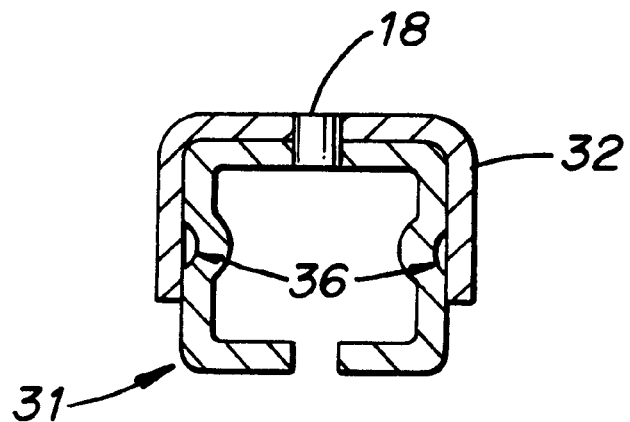
FIG. 3 is a cross-sectional view of the connection between the tissue stop and anvil of the prior art apparatus.

Referring to FIGS. 1, 2, and 3, a prior art surgical stapler 10 of the type disclosed in aforementioned U.S. Pat. No. 5,405,072 is illustrated which includes a first frame 11 including a support 12 which has a distal projection 13 for holding a disposable loading unit 20, a finger rest 14 and a handle 15. A cross pin 16 (FIG. 2) extends laterally across the first frame 11 between parallel plates 17 in proximity to the proximal end of the stapler 10. It should be noted that as used herein the terms longitudinal, lateral, and vertical refer to orientation with respect to the illustrated stapler and used relative to each other and not to any external fixed frame of reference. The longitudinal, lateral, and vertical directions are indicated by arrows L, S, and V, respectively, in FIG. 2.

The disposable loading unit 20 is removably insertable into the first frame 11 and includes a thrust knob 21, cam bars (not shown), knife blade 22, and a cartridge housing 23 for the staples. When the cam bars are advanced by pushing the thrust knob 21 distally, staple pushers within the housing 23 move the staples out of their respective slots to be crimped by the anvil when the staple legs are pushed into their respective anvil buckets.

The second frame 30, which is removably engageable with the first frame 11, comprises a relatively long anvil 31, a mounting bracket 32, a tip 33 fastened to the distal end of the anvil 31, a handle portion 34 pivotally connected to the bracket 32, and hinge plates 35 fastened to the handle 34. Bracket 32 is secured to anvil 31 by a rivet 18 disposed through an aperture in the top surfaces of the anvil 31 and bracket 32.

The anvil 31 has an elongated indentation 36 extending on each of the two lateral sides to offer increased resistance to bending, i.e. vertical deflection and thereby reduce misalignment of the frames. Trunnion 37 has side walls 38, each having a notch 39. The trunnion engages the proximal portion of the anvil (first) frame 11 such that the sides of walls 38 contact and abut corresponding parallel plates 17 in the first frame 11. Cross pin 16 engages notches 39. Because the anvil 31 includes indentations 36, the lateral side surfaces of the anvil 31 are not fully flush with the sides of bracket 32. In this prior known device, alignment is facilitated by the trunnion 37 and cross pin 16 in the rear of the apparatus as well as the bracket riveted to the anvil between the rear trunnion and tissue contacting jaws of the apparatus. The bracket and trunnion both have parallel planar surfaces designated by reference numerals 38a, 32a, respectively to aid in alignment. However, since all mating surfaces cannot be maintained parallel, and the trunnion is structurally stronger than the joint between the bracket and the anvil the trunnion takes over and determines alignment. However, the trunnion is located at the proximal end of the stapler, further from the staple line than the bracket.

Figure 4:
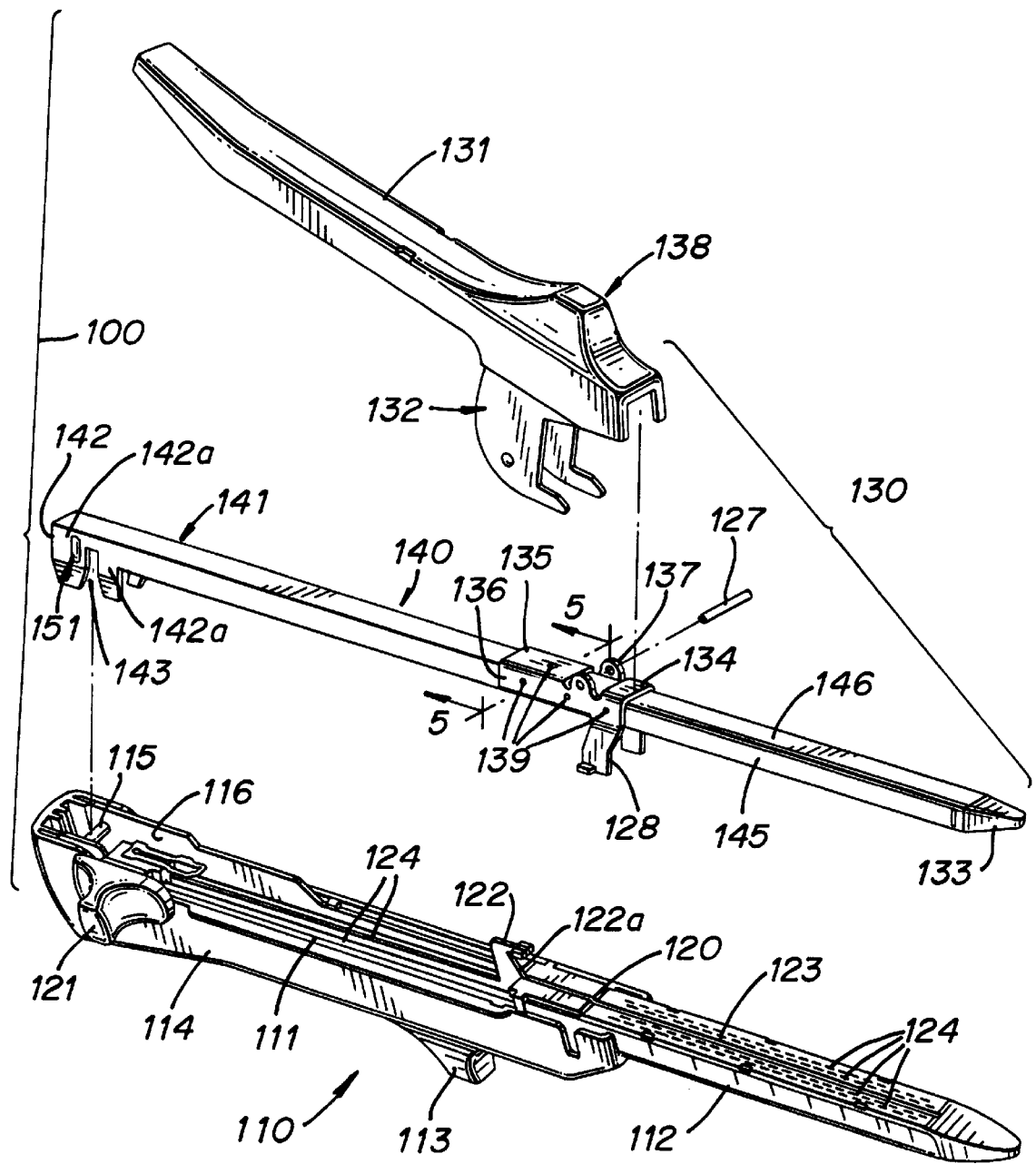
FIG. 4 is an exploded perspective view of the apparatus of the present invention.

Referring now to FIG. 4 a surgical stapler is illustrated which provides an alternative approach to maintain alignment of the jaws of the instrument. The stapler includes a first frame 110 and a second frame 130. The first frame 110 includes a support 111 mounted in a handle 114. The distal projection 112 of the support 111 is an elongated frame with a U-shaped cross section which receives the cartridge housing 123 of the disposable loading unit 120 (DLU). Handle 114 also includes a finger rest 113 to facilitate grasping of the instrument by the surgeon.

At the proximal end portion of the instrument the DLU support 111 also includes a cross pin 115 extending laterally across the instrument, and parallel plates for receiving the trunnion 141 of the anvil 140.

The disposable loading unit 120 includes a thrust knob 121 attached to cam bars (not shown) and a knife blade 122 having a distal cutting edge 122a. The cartridge housing 123 includes rows of slots 124 in which staples are positioned. Pusher plates (not shown) in the cartridge housing push the staples vertically out of the slots 124 and into the anvil buckets 148 (FIGS. 6, 8) in response to movement by the cam bars longitudinally through the cartridge housing 123.

The second (anvil) frame 130 includes a handle 131 with a finger rest 138. A pair of hinge plates 132 are fixedly mounted to the handle 131. The handle 131 is pivotally mounted to the hinge 137 of the mounting bracket 134 by means of a hinge pin (not shown).

Referring to FIGS. 6 and 8, anvil 140 is an elongated member fabricated from a stainless steel alloy and includes a back wall 146, two lateral side walls 145, and an inside wall 144 having a tissue contacting surface 147 and a knife slot 149 extending longitudinally along the length of the inside wall 144. Tissue contacting surface 147 includes two or more lengthwise extending rows of staple crimping buckets 148. In this embodiment it should be noted that the lateral sidewalls, unlike the prior art elongated anvil 31 discussed above, are flat and do not include the lengthwise indentation 36.

A tip 133, usually fabricated from plastic, is affixed to the distal end of the anvil to facilitate insertion into body tissue (FIG. 4).

The anvil 140 includes a trunnion 141 integral therewith, which includes spaced apart, downwardly extending walls 142 having flat side portion 142a bifurcated to form notches 143. When the first and second frames are assembled, notches 143 engage cross pin 115 and flat wall portions 142a contact and abut parallel plates 116.

In one embodiment (FIGS. 6 and 7) trunnion 141 includes a laterally projecting circular protuberance 150 on each exterior lateral side of side walls 142. In another embodiment (FIGS. 8 and 9) trunnion 141 includes a laterally projecting protuberance 151 on each exterior lateral side of side walls 142, protuberance 151 being elongated and linearly extending in a vertical direction.

By way of example, anvil 140 is preferably fabricated from stainless steel and can have a longitudinal extension, or length, of from about 10.30 inches to about 10.50 inches, a vertical extension, or height, of from about 0.35 inches to about 0.36 inches, and a lateral extension, or width, of from about 0.35 inches to about 0.36 inches. The length of the rows of staple crimping buckets 148 can be up to about 3.0 inches to 3.5 inches. The laterally projecting protuberances 150 and 151 can project laterally from about 0.015" to about 0.009" inches. Protuberance 151 can preferably have a vertical extension of about 0.500" to about 0.250" inches. These dimensions are illustrative and represent the size of but one embodiment of the apparatus. Anvils of other dimensions are also contemplated.

Figure 5:
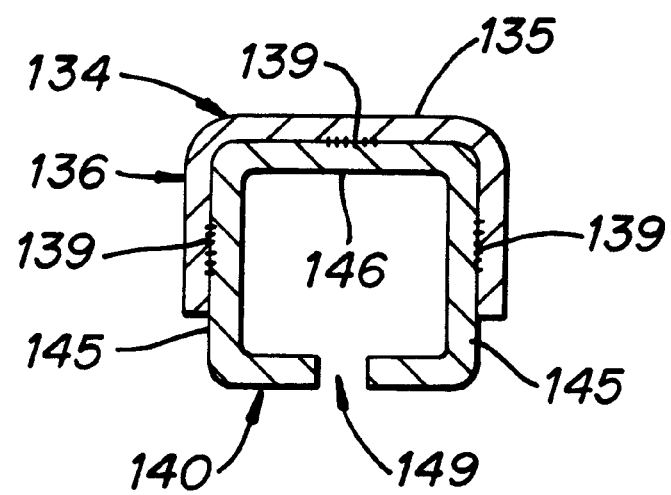
FIG. 5 is a cross-sectional view of the connection between the tissue stop and anvil of the apparatus of FIG. 4.

Referring to FIG. 4, the mounting bracket 134 provides means to pivotally connect handle 131 and anvil 140. Bracket 134 includes a hinge 137 having apertures through which hinge pin 127 is disposed. Back wall 135 and lateral side plates 136 provide support for bracket 134. Also, as a preferred but optional feature, bracket 134 can include depending plates 128 each having a distal edge which serves as a tissue stop to prevent body tissue from entering the area between the handles 131 and 114. As can be seen from FIG. 5, lateral side walls 145 of the anvil, and lateral side plates 136 of the bracket 134 are both flat and are dimensioned so as to fit flush against each other. Attachment of the bracket 134 to anvil 140 is accomplished by several spaced apart spot welds 139 along the respective lateral side plates 136 and side walls 145, and optionally back walls 135 and 146 as well. Preferably at least two, and more preferably three, spot welds are performed on each side. Close mating of the surfaces and multiple weld points along the lateral sides increases the stability of the attachment.

Moreover, the protuberances 150, 151 on the trunnion allow the trunnion to pivot slightly, thereby tending to shift the alignment function to bracket 134, which is connected to anvil 140 by an attachment of greater stability. Thus, since bracket 134 is structurally stronger than trunnion 141, the bracket 134, which is closer to the staple line, will take over and handle alignment. Use of the anvil and bracket structures described also advantageously enables longer anvils to be constructed while maintaining satisfactory alignment. The elongated indentation of the prior art device described above, the purpose of which is to improve alignment by increasing bending resistance, can be eliminated and good alignment still maintained. Fabrication is thereby made easier and less expensive.

It will be understood that various modifications can be made to the embodiments disclosed herein. For example, the trunnion can be located on the first frame containing the staples with the transverse pin on the second (anvil) frame. Therefore the above description should not be construed as limiting but merely as exemplifications of preferred embodiments. Those skilled in the arts will envision other modifications within the scope and spirit of the claims appended hereto.

What is claimed is:

1. An apparatus for applying surgical staples, which comprises:
    a) a first frame having a proximal end portion and a distal end portion, and including a support connected to a first handle; and
    b) a second frame releasably engaged with the first frame, the second frame including an elongated anvil and a bracket fixedly attached to the anvil, a second handle pivotally mounted to the bracket, the anvil having a proximal end portion and a distal end portion, the proximal end portion of the anvil having a trunnion portion which includes two spaced apart walls, each wall having an outward facing surface and a laterally projecting protuberance on a portion of the planar surface, and wherein the anvil includes at least one planar lateral side and the bracket includes at least one planar lateral side parallel to and in flush contact with the planar lateral side of the anvil and fixedly attached thereto.

2. The apparatus of claim 1 wherein the portions of the outward facing surfaces on which the laterally projecting protuberances are located are substantially planar.

3. The apparatus of claim 1 wherein the first frame includes a laterally extending cross pin, and the two spaced apart walls of the trunnion portion each include a notch for receiving a respective portion of the cross pin.

4. The apparatus of claim 1 wherein the laterally projecting protuberance is circular.

5. The apparatus of claim 1 wherein the laterally projecting protuberance is elongated.

6. The apparatus of claim 5 wherein the elongated laterally projecting protuberance is oriented in a vertical direction with respect to the anvil.

7. The apparatus of claim 1 wherein the at least one lateral side of the bracket and the at least one lateral side of the anvil are attached to each other by at least one spot weld.

8. The apparatus of claim 1 wherein the at least one lateral side of the bracket and the at least one lateral side of the anvil are attached to each other by at least three spot welds.

9. The apparatus of claim 1 wherein the bracket includes at least one tissue stop.

10. The apparatus of claim 1 further including a disposable loading unit mounted within the support in the first frame which includes a plurality of staples stored within respective slots in a housing mounted to the support, a plurality of staple pushers mounted within the slots for pushing the staples out of the slots, first and second bars having distal camming edges for activating the staple pushers, the bars being movably mounted to the support, a third bar having a knife blade, and a thrust knob operatively connected to the first, second, and third bars and slidably mounted within the support frame for distally advancing the first, second, and third bars.

11. The apparatus of claim 1 wherein the first frame includes two parallel walls, each having an inwardly facing flat surface removably contacted by a respective one of the laterally projecting protuberances of the trunnion.

12. An apparatus for applying surgical staples which comprises:
    a) a first frame having a proximal end portion and a distal end portion;
    b) a transverse pin supported at the proximal end portion of the first frame; and
    c) a second frame removably mountable to the first frame and having a proximal end portion and a distal end portion, the proximal end portion including a pair of spaced apart downwardly extending surfaces, each surface being bifurcated to form a notch to engage the transverse pin, and each surface including a laterally projecting protruberance configured to engage an inner surface of the first frame.

13. The apparatus of claim 12, further comprising a bracket rigidly mounted to the second frame distal of the proximal end portion.

14. The apparatus of claim 13, wherein the bracket is spot welded to the second frame in at least several points so that the mounting of the bracket to the second frame is structurally stronger than the engagement between the downwardly extending surfaces and the first frame to reduce movement of the bracket relative to the second frame during clamping of the tissue.

15. The apparatus of claim 14, further comprising a plurality of anvil depressions on the second frame.

16. An anvil assembly for use in an apparatus for applying surgical fasteners to body tissue, which comprises:
    an elongated anvil member having first and second lateral side wall, and a tissue contacting third wall, the elongated member having a distal end portion and a proximal end portion, the proximal end portion having a trunnion with first and second exterior side surfaces, each exterior side surface having means for distally shifting alignment function, said means including a laterally projecting protuberance for engaging a corresponding flat wall on a frame for engaging the anvil assembly.

17. The anvil assembly of claim 16 wherein the laterally projecting protuberance is circular.

18. The anvil assembly of claim 17 wherein the laterally projecting protuberance is elongated.

19. The anvil assembly of claim 18 wherein the elongated laterally projecting protuberance is oriented in a vertical direction with respect to the elongated anvil member.

20. The anvil assembly of claim 16 further including a bracket attached to the elongated anvil member, the bracket having first and second side plates each being configured for abutting engagement with a respective one of the first and second lateral side walls of the anvil member, the first and second side plates and corresponding first and second side walls being substantially flat and in flush contact with each other.

21. The anvil assembly of claim 20 wherein the bracket first and second side plates and corresponding abutting first and second side walls of the anvil member are fastened together by spot welding in plural locations.

* * * * *